United States Patent [19]

Hird et al.

[11] Patent Number: 5,366,872
[45] Date of Patent: Nov. 22, 1994

[54] TEST KITS AND METHODS FOR EVALUATING STERILIZATION CYCLES

[75] Inventors: Robert F. Hird, Pleasant Hill; Edward F. Cosgrove, Danville, both of Calif.

[73] Assignee: Envirocon International Corporation, Concord, Calif.

[21] Appl. No.: 989,797

[22] Filed: Dec. 9, 1992

[51] Int. Cl.$^5$ .................. C12Q 1/22; G01N 21/00
[52] U.S. Cl. ......................... 435/31; 435/4; 435/34; 435/810; 422/31; 422/61
[58] Field of Search ............... 435/31, 4, 34, 810; 422/31, 61

[56] References Cited

U.S. PATENT DOCUMENTS

| | | | |
|---|---|---|---|
| 4,388,233 | 6/1983 | Bissell et al. | 549/288 |
| 4,591,554 | 5/1986 | Koumura et al. | 435/34 |
| 4,803,162 | 2/1989 | Smith et al. | 435/34 |
| 5,073,488 | 12/1991 | Matner et al. | 435/31 |

OTHER PUBLICATIONS

Vasley et al, *Applied and Environmental Microbiology*, vol. 58, No. 2, pp. 969-973, 1986.
(1986) A. Peter Snyder, et al., *Applied and Environmental Microbiology*, 51(5):969-973, "Pattern Recognition Analysis of In Vivo Enzyme-Substrate Fluorescence Velocities in Microorganism Detection and Identification".
(1992) Donald Vesley, et al., *Applied and Environmental Microbiology*, 58(2):717-719, "Fluorimetric Detection of a *Bacillus stearothermophilus* Spore-Bound Enzyme, α-D-Glucosidase, for Rapid Indication of Flash Sterilization Failure".
(1986) Propper Product Literature, "Duo-Spore, Biological indicators for monitoring effectiveness of sterilization procedures. For steam (gravity displacement of high vacuum), ethylene oxide gas or dry heat." (Long Island City, NY 11101.).
(1990) 3M Health Care Technical Report for Infection Control Products, "1291 Attest Rapid Readout Biological Indicator Technical Report." (St. Paul, MN 55144-1000.).
(1990) ATI, a Division of PyMaH Corp. Product Instructions, "ATI Disposable Biological Test Pack For Steam Sterilizers." (Somerville, NJ 08876.).

*Primary Examiner*—Michael G. Wityshyn
*Assistant Examiner*—Abdel A. Mohamed
*Attorney, Agent, or Firm*—Townsend and Townsend Khourie and Crew

[57] ABSTRACT

Methods and kits are provided for detecting viable bacteria or microorganisms at the completion of a sterilization cycle using rapid biological detection systems. The results of the detection systems can be read visually by non-technical personnel within one hour of the sterilization cycle at room temperature, resulting in a quick, cost-effective, and easy-to-use method or diagnostic kit.

13 Claims, 1 Drawing Sheet

5,366,872

TEST KITS AND METHODS FOR EVALUATING STERILIZATION CYCLES

BACKGROUND OF THE INVENTION

1. Field of the Invention

The invention is in the field of detecting viable bacteria or microorganisms, if any, upon completion of a sterilization cycle, using rapid biological detection systems. Therefore, the invention can be used to determine whether bacteria are destroyed in a sterilization cycle.

2. Description of the Background Art

The detection of remaining viable bacteria or microorganisms after a sterilization cycle is important in the prevention of infection and the spread of diseases. Before using instrumentation in surgical and dental procedures, personnel need to know if the instruments have been properly sterilized, usually immediately after the sterilization cycle has been completed. Unfortunately, conventional tests require a lengthy time and complicated process before the sufficiency of the cycle can be evaluated.

For example, a biological indicator can be included in the sterilization run, but typically the indicator consists of bacteria that must be grown in culture media at an elevated temperature for a period of up to 7 days, usually about one to two days, before the adequacy of the sterilization can be determined. At the end of the culture period, the viability of any bacteria remaining after the sterilization is determined by measuring bacterial growth. If there is no growth, then the sterilization cycle was complete and the bacteria adequately destroyed. If growth occurs, then the sterilization cycle was faulty or incomplete.

Most of the conventional growth tests are conducted at test facilities outside the medical or dental offices, which add to the delay and cost in obtaining the results. Also, the bacteria may be transferred from its sterilization container to the culture media, increasing the chances of contamination and mishandling. Oftentimes the instruments contained within the sterilization cycle cannot be quarantined and must be used before the results of the bacterial growth test are known. In situations where the instruments have been utilized and the sterilization cycle was inadequate, personnel must locate the patient for proper treatment to control the possibility of infection.

Therefore, it is highly desirable to determine the results of a sterilization cycle within a short period of time, such that the sterility of the instruments is known before their use on a patient. It also is desirable for the results to accurately reflect the completeness of the sterilization run, in particular, especially as to the inactivation or destruction of the viable bacteria or microorganisms.

SUMMARY OF THE INVENTION

The present invention allows for the results of a sterilization cycle or run to be determined within about 10 minute to about one hour of its completion, using a rapid biological test or assay that can be performed at about room temperature within or nearby the sterilization facility without instrumentation and without incubation at elevated temperatures.

A method of detecting the presence of viable microorganisms after a sterilization cycle is provided which comprises the steps of: (a) exposing a source of the viable microorganisms to the sterilization cycle; (b) contacting the viable microorganisms after the sterilization cycle with an aqueous buffer and a substrate which is specific for and reacts with the viable microorganisms at about room temperature to form a substrate-microorganism complex; (c) adding a color developer which is specific for and reacts with the substrate-microorganism complex to generate a color in the presence of viable microorganisms at about room temperature; (d) determining the existence of color by visual means in about ten minutes to about one hour; and (e) correlating the existence of color with the presence of viable microorganisms.

In particular, the invention is directed toward the detection of one or more viable bacteria types, such as *Bacillus stearothermophilus* spores and *Bacillus subtilis* spores, on a filter.

Also provided is a method of detecting the presence of viable microorganisms after the completion of a sterilization cycle, wherein a source of viable microorganisms is exposed to the sterilization cycle, is contacted with a substrate specific for the viable microorganisms after the sterilization cycle to form a substrate-microorganism complex, and then is contacted with a means for detecting the substrate-microorganism complex as an indication of the presence of viable microorganisms, the improvement comprising: (I) using an aqueous buffer and a substrate which substrate forms a complex with viable microorganisms at about room temperature; (II) using a color developer which reacts with the substrate-microorganism complex at about room temperature as the means for detecting the complex, such that the existence of color can be determined by visual means in about 10 minutes to about one hour; and (III) correlating the existence of color with the presence of viable microorganisms.

Further provided is a method for diagnosing a major and marginal sterilization failure in about 10 minutes to about one hour by detecting viable microorganisms after the completion of a sterilization cycle comprising the steps of: (i) constructing a filter with four test areas wherein the first test area is used to diagnose a major sterilization failure, the second test area is used to diagnose a marginal sterilization failure, the third test area is used as a positive control, and the fourth test area is used as a negative control; (ii) impregnating a source of viable microorganisms onto the filter within the first and second test areas and impregnating a source of a positive control onto the filter within the third test area; (iii) exposing the impregnated filter to a sterilization cycle; (iv) removing the filter at the completion of the sterilization cycle; (v) contacting all four test areas with an aqueous buffer and a substrate specific for viable microorganisms or viable microorganism by-products at about room temperature, which substrate forms a complex with the microorganisms or by-products; (vi) after about 10 minutes, adding a color developer to the first test area, which developer reacts with the substrate-microorganism complex to generate a color in the presence of viable microorganisms or viable microorganism by-products at about room temperature; (vii) visually examining the filter to determine the existence of color in the first test area; (viii) diagnosing the existence of color in the first test area as a major sterilization failure; (ix) if no color exists in the first test area at the end of about 10 minutes, adding the color developer to the remaining three wells after about one hour, which developer also reacts with the positive control to generate a color at about room temperature; and visually examining the filter to determine the existence of color in the second, third, and fourth test areas; (x) diagnosing the existence of color in the second test area as a marginal sterilization failure; and (xi) diagnosing the lack of color in the third test area and/or the existence of color in the fourth test area as a reagent or test failure.

Diagnostic kits are provided for detecting the presence of viable microorganisms after a sterilization cycle comprising: (a) a filter containing the viable microorganisms; (b) an aqueous buffer; (c) a substrate specific for the viable microorganisms, which reacts with the viable microorganisms or viable microorganism by-products at about room temperature; and (d) a color developer specific for the substrate, which developer reacts with the substrate in the presence of viable microorganisms or viable microorganism by-products at about room temperature, and can be detected by visual means.

BRIEF DESCRIPTION OF THE FIGURES

The figures described below are selected examples of the various aspects of this invention, but should not be construed as limiting.

DESCRIPTION OF SPECIFIC EMBODIMENTS

Figure 1A:
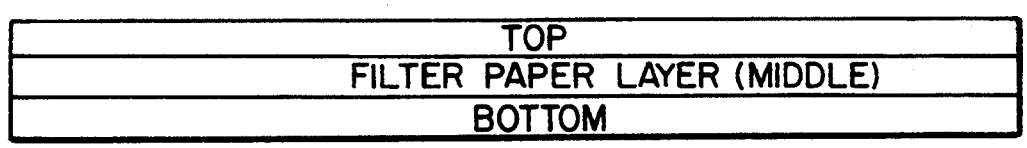
FIG. 1 depicts three views of a test strip device A side view of the three layered device is shown in FIG. 1A.
FIG. 1C is a view from the top depicting three holes or ports, designated 1, 2, and 3, which are punched out of the top layer.
FIG. 1B, an open view from the side of the device, depicts; filter contained within the holder such that the holes expose three regions or areas on the filter.
Figure 1B:
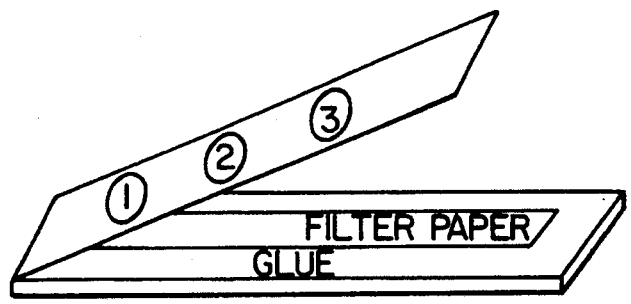
Figure 1C:
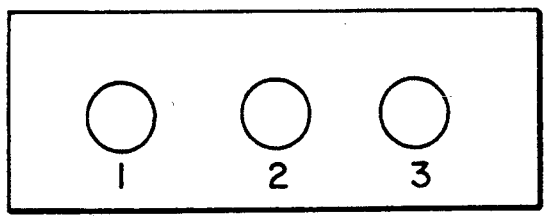
Figure 2:
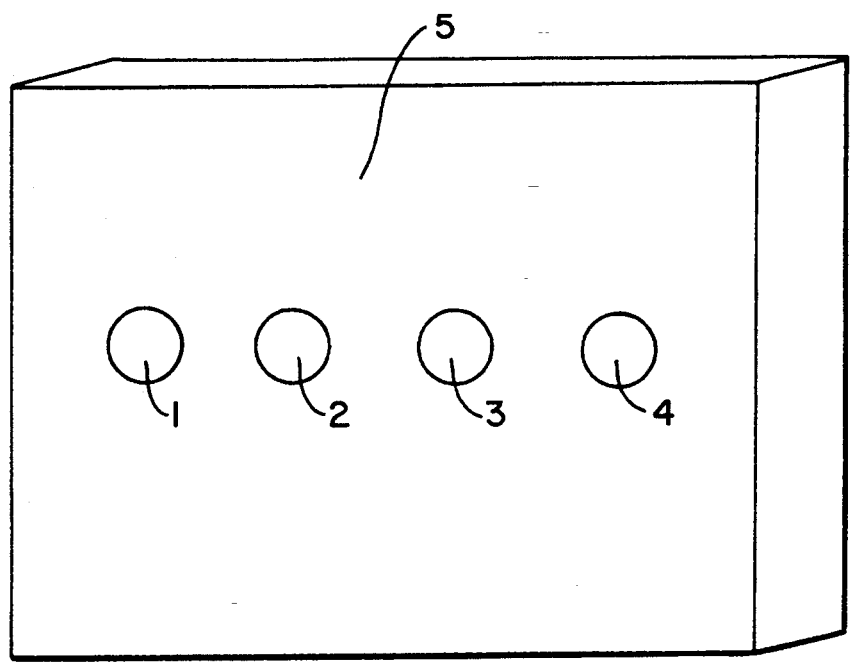
FIG. 2 shows the top view of a test strip device consisting of a cardboard holder (5) with four holes or ports exposing four regions or areas on a filter. Test area (1) is used to diagnose a major sterilization failure; test area (2) is used to diagnose a marginal sterilization failure; test area (3) is used as a positive control; and test area (4) is used as a negative control.

The claimed invention eliminates the problems found with the conventional or existing test systems by being quick, cost-effective, and easy to use. In addition, it permits a visual reading of the results by non-technical personnel within about 10 minutes to about one hour of the sterilization run and, therefore, does not require any instrumentation to interpret the results. No background noise is generated using the invention that must be eliminated or subtracted before interpreting the results of the present biological test or system as is the case with other conventional tests, especially those that utilize fluorescence.

The system of the invention does not require the transfer of the bacteria or biological material from the sterilized container to a culture medium, which entails possible contamination or mishandling. Nor does it require an elevated temperature, such as during incubation, in order to effectively measure the existence of bacterial cells. Furthermore, the results can be read visually without manipulation by the handler and without additional steps. This type of test lowers the possibility of incorrect results, such as false positives, and substantially lowers the cost of verifying the completeness of the sterilization cycle.

The invention methods detect the presence of viable microorganisms after the completion of a sterilization cycle wherein a source of the microorganisms is exposed or subjected to the sterilization cycle and its viability after the completed cycle is determined by a visual system using a substrate and color developer at about room temperature.

The sterilization means used in the cycle or run can be any conventional sterilization procedures, such as high temperature, saturated steam, dry heat, radiation, gas plasma, ethylene oxide, or other gaseous or chemical entities, and the like, under conditions normally used with these procedures. Preferably, the sterilization means utilized will be steam. Typically, the sterilizer is run from about 3 minutes to about 30 minutes at a temperature from about 250 to about 270° F., depending upon the type of sterilizer utilized. (See USP XXII 1990.)

The types of microorganisms or bacteria used in this invention to determine the sufficiency of the sterilization cycle include Bacillus and Clostridia species, such as *Bacillus stearothermophilus, Bacillus pumilus* and *Bacillus subtilis*, and the like. See USP XXII 1990. The preferred type is bacteria of the Bacillus family. Usually the source of the microorganism is in the form of a spore, since that form is the most resistant stage in the bacterial life cycle and therefore, more difficult to kill. In addition, more than one type of microorganism can be detected using this invention.

In order to detect the viability of a microorganism after the sterilization cycle, a substrate is utilized in conjunction with a color developer which reacts with the microorganism or a by-product, such as an enzyme, and with the substrate when the substrate and microorganism are complexed. Usually an enzyme within a live or viable microorganism recognizes the substrate and, under hydrolysis, causes a cleavage within the substrate to release a tag or marker. This marker or tag, in turn, binds with the color developer to form the color for detection. A sufficient amount of the substrate and color developer must be used to react with the microorganisms and the components must interact for a sufficient length of time to detect viable organisms. The concentration or amount used and the time period for reaction will depend upon the particular configuration of the test and its components, as well as the type of microorganism or microorganisms being detected. Other ingredients or materials can be used in conjunction with the substrate, color developer, and the microorganism, such as buffers, solutions, and the like.

The substrate can be any hydrolytic substance or mixture of substances acted upon by an enzyme or microorganism by-product within a microorganism or bacteria, indicating viability of the microorganism or by-product. The interaction of the substrate and the microorganism results in a modification of the substrate to release the tag or marker, which can be a luminescent, fluorescent, colored, or radioactive material. The substrate tag further reacts with the color developer to give the resulting color in the assay. Substrates used in this invention include: alanine-alanine-6-aminoquinalone; Bci-glucoside (5-bromo-4-chloro-3-indolyl-beta D-glucopyranoside); 4-methylumbelliferyl-a-D-glucoside (4-methylumbelliferyl-a-D-glucopyranoside); 7-hydroxy-4-methylcoumarin; 7-hydroxy-4-trifluoromethylcoumarin; L-pyroglutamic acid-7-amino-4-methylcoumarin; L-pyroglutamic acid-7-amino-4-trifluoromethylcoumarin; L-pyroglutamic acid-p-nitroanilide; L-pyroglutamic acid-b-naphthylamide; and the like, with alanine-alanine-6-aminoquinalone being preferred.

Useful color developers include: para-dimethylaminocinnamaldehyde, 5-nitrosalicyaldehyde (5-NSA), benzaldehyde, p-nitrobenzaldehyde, and the like, with para-dimethylaminocinnamaldehyde being preferred.

The microorganism or by-product and the substrate are reacted in an aqueous buffer solution, such as a tris(hydroxymethyl)aminomethane hydrochloride solution, and the like. These buffer solutions must be compatible with the substrates and the microorganisms, and must not affect their interaction with the substrate.

It is an advantage of the present invention that the methods can be performed under room temperature, such as from about 24° C. to about 30° C. and under room conditions rather than at elevated temperatures.

The biological test or assay methods of this invention can be performed on a porous or absorbent filter, membrane, matrix, or solid support made of any suitable inert material. The filter should not dissolve the reactants or components of the method and it should have negligible non-specific attraction for these components. However, it must be able to act as a reaction surface for the components and the microorganisms, such that the microorganisms and certain of the components can be fixed, bound, complexed, immobilized or impregnated on, or within, the filter. (Any material exposed to the sterilization run must be of sufficient stability to withstand the sterilization conditions.) Other components can be added as reagents during the assay method. Therefore, although the filter is porous, it must be able to retain or bind the required components through physical or chemical means. In addition, the filter must facilitate the interaction or reaction of the components and microorganisms in order to properly conduct the assay method.

The filter can be a matrix or solid support usually composed of a mat of compressed fibers, such as a mat of glass or synthetic fibers or a porous paper mat. It also may be constructed of other porous materials known to those skilled in the art, such as sintered glass, ceramics, synthetic spongy materials, synthetic polymers, gels, mixtures of these substances, and the like, with the preferred material being paper or nitrocellulose.

The filter can be constructed in a variety of shapes and sizes, such as strips, sheets, plates, cylinders, dipsticks, and the like, depending upon the particular assay format desired. The filter is from about 0.1 to about 0.5 mm (millimeters) in thickness with a retention range from about 2 to about 5 $\mu$(microns). It is necessary that the pore size be small enough to prevent the components and/or microorganisms from being completely passed through the filter and to allow the components and microorganisms to interact. The preferred filter thickness is about 0.36 mm with a retention size of about 2 $\mu$.

One skilled in the art will appreciate that the filter can be protected by a cover, holder and the like, such that only certain regions of the filter are exposed. The cover or holder can be comprised of many materials, such as heavy paper, cardboard, plastic, glass, or any other rigid or semi-rigid material and the like, so long as the cover or holder does not impact upon the biological test results and is not adversely affected by the sterilization cycle. Preferably, the cover will be cardboard or plastic.

On the filter there can be one or multiple regions or areas, which are used in the biological assay. The regions on the filter can be constructed to contain single or multiple microorganisms as well as other components. In addition, the filter can contain one or more positive and/or negative test areas, which can be used to evaluate whether the method was properly conducted. The regions can be a variety of shapes and sizes depending upon the format desired. It is important that the regions remain distinct from each other in order to prevent contamination or migration from one region to the other. Oftentimes, the cover or holder can be used to isolate these filter regions or areas.

Upon completion of the test method or assay, the filter can be dried, stored, and/or discarded. If the filter is stored, it should be under storage conditions that are proper for the retention of the results.

The invention also comprises diagnostic kits wherein the filter, components, and microorganisms are part of the kit. Included as ancillary reagents can be buffers, diluents, standards, instructions, and the like. In most cases, the kits are complete for use after the sterilization cycle and contain the material to be included in the sterilization run. The present invention is illustrated by the following examples. These examples are not intended to limit the scope of the invention.

Materials:

The following materials are prepared for use:

Buffer:

| | |
|---|---|
| Tris(hydroxymethyl)(amino methane hydrochloride) | 0.10M (Molar) |
| Thioglycolic Acid | 0.01M |
| Triton X-100 (non-ionic detergent) | 0.04M |

The buffer components are dissolved in deionized water and the pH is adjusted to about 8.3±0.2 with 1M sodium hydroxide.

Color Developer:

| | |
|---|---|
| Para-dimethylaminocinnamaldehyde | 6.0 gm (grams) |
| Hydrochloric acid (37%) | 100.0 ml (milliliter) |
| Deionized water | 900.0 ml |

The color developer components are mixed and the resulting pH is about 2.5±0.5.

25 Positive Control:

| | |
|---|---|
| 6-aminoquinalone | 0.025 gm |
| Methanol | 25.000 ml |
| Buffer | 100.000 ml |

The components of the control are mixed together.

Substrate Solution: The substrate solution is prepared at a concentration of about 0.005 mg/ml (milligrams per milliliter) using:

| | |
|---|---|
| N,N-Dimethyl-formamide | 5.000 ml |
| Methanol | 200.000 ml |
| Substrate | 0.100 gm | wherein the substrate is selected from: BCI-glucoside (5-bromo-4-chloro-3-indolyl-beta-D-glucopyranoside); 4-methylumbelliferyl-a-D-glucoside (4-methylumbelliferyl-a-D-glucopyranoside); 7-hydroxy-4-methylcoumarin; 7-hydroxy-4-trifluoromethylcoumarin; L-pyroglutamic acid-7-amino-4-methylcoumarin; L-pyroglutamic acid-7-amino-4-trifluormethylcoumarin; L-pyroglutamic acid-p-nitroanilide; L-pyroglutamic acid-b-naphthylamide; or alanine-alanine-6-aminoquinalone.

EXAMPLE 1

A cardboard holder is prepared with three holes punched out of it. Into the holder is placed a filter paper, such that three areas of the filter are exposed through the holes.

Bacillus stearothermophilus spores are impregnated onto the filter paper at a concentration of about $10^4$ to about $10^7$ spores for a 7/16 inch diameter and allowed to dry. The spores are located only within a designated area, called Well #1. A second area, called Well #2, is left blank. A third area on the filter paper, designated as Well #3, is impregnated with the Positive Control at a concentration of 0.2 mg/ml.

The cardboard holder containing the prepared filter paper is placed in a glassine bag and sealed. The bag then is placed in the sterilizer for the specified sterilization cycle. Upon completion of the cycle, the bag is removed from the sterilizer and the cardboard holder with filter paper is removed from the bag. One drop of Buffer and one drop of Substrate Solution, containing alanine-alanine-6-aminoquinalone, are added to each well. After approximately 30 minutes at about room temperature (about 24 to 30° C.), one drop of the Color Developer is added to each well.

After about one minute, the filter paper is evaluated by reviewing the color in each well. A purple color in Well #1 indicates an incomplete sterilization cycle, since Bacillus survived the cycle and remain viable; whereas no color in Well #1 indicates a complete and successful sterilization run. Since Well #2 is a negative control, no color should be found. Any color in Well #2 is indicative of a reagent or testing failure. Since Well #3 is a positive control, a purple color should develop quickly upon addition of the Color Developer. A lack of color in Well #3 is indicative of a reagent or testing failure.

Therefore, a successful sterilization cycle will result in a filter strip with a purple color in Well #3, but colorless in Wells #1 and #2. If color is found in Well #1, then the instruments within the sterilization run should not be used, since the run was inadequate for complete sterilization.

EXAMPLE

Bacillus subtilis spores are impregnated onto filter paper within two test areas, called Well #1 and #2, at a concentration of about 104 to about 107 spores for a 7/16 inch diameter and allowed to dry. A third region on the filter, called Well #3, is impregnated with the Positive Control at a concentration of 0.2 mg/ml. A fourth region on the test area, called Well #4, is left blank to act as a negative control.

After the well areas are prepared, the filter paper is covered with a plastic or cardboard holder containing four openings or holes. These openings are located above the four wells, directly exposing the entire well areas on the filter paper.

The cardboard holder containing the prepared filter paper is placed in a glassine bag and sealed. The bag then is placed in the sterilizer for the specified sterilization cycle. Upon completion of the cycle, the bag is removed from the sterilizer and the cardboard holder with filter paper is removed from the bag. One drop of Buffer and one drop of Substrate Solution, containing alanine-alanine-6-aminoquinalone, are added to each well. After about 10 minutes, one drop of the Color Developer is to Well #1.

After about one minute, the filter paper is evaluated by reviewing the color in Well #1. A purple color in Well #1 indicates a major sterilization failure, since large quantities of Bacillus survived the cycle and remain viable.

If Well #1 is colorless, Color Developer is added to the remaining three wells after about one hour and the wells are examined visually. If any color develops in Well #2, then the sterilization cycle was incomplete. Since Well #3 is a positive control, a purple color should develop quickly upon addition of the Color Developer in all tests; whereas, Well #4 should remain colorless, since it is a negative control. A lack of color in Well #3 and/or the presence of color in Well #4 is indicative of a reagent or testing failure.

Therefore, a successful sterilization cycle will result in a filter strip with a purple color in Well #3, but no color in Wells #1, #2, and #4. If color is found in Well #1 or #2, then the instruments within the sterilization run should not be used, since the run was inadequate for complete sterilization.

All publications and other references or patent documents cited herein are incorporated by reference. It is to be understood that the above description is intended to be illustrative and not restrictive. Many embodiments will be apparent to those skilled in the art upon reviewing the above description. The scope of the invention, therefore, should be determined with reference to the appended claims, along with the full scope of equivalents to which such claims are entitled.

Although the foregoing invention has been described in some detail by way of illustration and example, for purposes of clarity of understanding, it will be obvious that certain changes and modifications may be practiced within the scope of the appended claims.

What is claimed is:

1. A method of detecting the presence of viable microorganisms after a sterilization cycle comprising the steps of:
   (a) exposing a source of viable microorganisms to a sterilization cycle;
   (b) contacting the viable microorganisms after the sterilization cycle with an aqueous buffer and a substrate which is specific for and reacts with the viable microorganisms at about room temperature to form a substrate-microorganism complex;
   (c) adding a color developer which is specific for and reacts with the substrate-microorganism complex to generate a color in the presence of viable microorganisms at about room temperature;
   (d) determining the existence of said color by visual means in about ten minutes to about one hour; and
   (e) correlating the existence of said color with the presence of viable microorganisms.

2. The method of claim 1 wherein the viable microorganisms are bacteria.

3. The method of claim 2 wherein the viable microorganisms are selected from the group consisting of Bacillus stearothermophilus spores and Bacillus subtilis spores.

4. The method of claim 1 wherein the substrate is selected from the group consisting of: alanine-alanine-6-aminoquinalone; BCI-glucoside (5-bromo-4-chloro-3- indolyl-beta-D-glucopyranoside); 4-methylumbelliferyl-a-D-glucoside (4-methylumbelliferyl-a-D-glucopyranoside); 7-hydroxy-4-methylcoumarin; 7-hydroxy-4-trifluoromethylcoumarin; L-pyroglutamic acid-7-amino-4-methylcoumarin; L-pyroglutamic acid-7-amino-4-trifluormethylcoumarin; L-pyroglutamic acid-p-nitroanilide; and L-pyroglutamic acid-b-naphthylamide.

5. The method of claim 1 wherein the color developer is selected from the group consisting of para-dimethylaminocinnamaldehyde, 5-nitrosalicyaldehyde, benzaldehyde, and p-nitrobenzaldehyde.

6. The method of claim 1 wherein the sterilization cycle uses a sterilization means selected from the group consisting of high temperature, saturated steam, dry heat, radiation, gas plasma, and ethylene oxide.

7. The method of claim 1 wherein the room temperature is from about 24° C. to about 30° C.

8. The method of claim 1 wherein the aqueous buffer consists of tris (hydroxymethyl)(aminomethane hydrochloride), thioglycolic acid, and a non-ionic detergent in deionized water at a pH of about 8.3.

9. The method of claim 1 wherein the source of the viable microorganisms is impregnated onto a filter.

10. The method of claim 1 wherein the substrate reacts with viable enzymes within the microorganisms.

11. In a method of detecting the presence of viable microorganisms after the completion of a sterilization cycle, wherein a source of viable microorganisms is exposed to the sterilization cycle, is contacted with a substrate specific for the viable microorganisms after the sterilization cycle to form a substrate-microorganism complex, and then is contacted with a means for detecting the substrate-microorganism complex as an indication of the presence of viable microorganisms, the improvement comprising:
  (I) using an aqueous buffer and a substrate which substrate forms a complex with viable microorganisms at about room temperature;
  (II) using a color developer which reacts with the substrate-microorganism complex to generate a color at about room temperature as the means or detecting the complex, determining the existence of said color by visual means in about 10 minutes to about one hour; and
  (III) correlating the existence of said color with the presence of viable microorganisms.

12. A method or diagnosing a major sterilization failure in about 10 minutes and a marginal sterilization failure in about one or by detecting viable microorganisms or viable microorganism enzymes after the completion of a sterilization cycle comprising the steps of:
  (i) constructing a filter with four test areas wherein a first test area is used to diagnose a major sterilization failure, a second test area is used to diagnose a marginal sterilization failure, a third test area is used as a positive control, and a fourth test area is used as a negative control;
  (ii) impregnating a source of viable microorganisms onto the filter within the first and second test areas and impregnating a source of a positive control onto the filter within the third test area;
  (iii) exposing the impregnated filter to a sterilization cycle;
  (iv) removing the filter at the completion of the sterilization cycle;
  (v) contacting all four test areas with an aqueous buffer and a substrate specific or viable microorganisms or viable microorganism enzymes at about room temperature, which substrate forms a complex with the microorganisms or enzymes;
  (vi) after about 10 minutes, adding a color developer to the first test area, which developer reacts with the complex to generate a color in the presence of viable microorganisms or viable microorganism enzymes at about room temperature;
  (vii) visually examining the filter to determine the existence of said color in the first test area;
  (viii) diagnosing the existence of said color in the first test area as a major sterilization failure;
  (ix) if no color exists in the first test area at the end of about 10 minutes, adding the color developer to the remaining three wells after about one hour, which developer also reacts with the positive control to generate said color at about room temperature; and visually examining the filter to determine the existence of said color in the second, third, and fourth test areas;
  (x) diagnosing the existence of said color in the second test area as a marginal sterilization failure; and
  (xi) diagnosing the lack of said color in the third test area as a reagent failure and the existence of said color in the fourth test area as a test failure.

13. A diagnostic kit for detecting the presence of viable microorganisms after a sterilization cycle comprising.
  (a) a filter containing viable microorganisms;
  (b) an aqueous buffer;
  (c) a substrate specific for the viable microorganisms, which reacts with the viable microorganisms or viable microorganism enzymes at about room temperature; and
  (d) a color developer specific for the substrate, which developer reacts with the substrate in the presence of viable microorganisms or viable microorganism enzymes to generate a color at about room temperature which color can be detected by visual means.

* * * * *

Adverse Decisions In Interference

Patent No. 5,366,872, Robert F. Hird, Edward F. Cosgrove, TEST KITS AND METHODS FOR EVALUATING STERILIZATION CYCLES, Interference No. 103,606, final judgment adverse to the patentees rendered February 25, 1998, as to claims 1-13.
*(Official Gazette June 2, 1998)*